(12) United States Patent
Norgren

(10) Patent No.: US 8,492,002 B2
(45) Date of Patent: Jul. 23, 2013

(54) TITANIUM-BASED ALLOY

(75) Inventor: Susanne Norgren, Huddinge (SE)

(73) Assignee: Sandvik Intellectual Property AB, Sandviken (SE)

( * ) Notice: Subject to any disclaimer, the term of this patent is extended or adjusted under 35 U.S.C. 154(b) by 785 days.

(21) Appl. No.: 12/585,744

(22) Filed: Sep. 23, 2009

(65) Prior Publication Data
US 2010/0086794 A1  Apr. 8, 2010

(30) Foreign Application Priority Data

Sep. 23, 2008  (EP) .................................... 08164918

(51) Int. Cl.
*B32B 15/04* (2006.01)
*C22C 14/00* (2006.01)
*C22F 1/18* (2006.01)

(52) U.S. Cl.
USPC ......... 428/472.1; 420/417; 148/421; 148/669

(58) Field of Classification Search
None
See application file for complete search history.

(56) References Cited

U.S. PATENT DOCUMENTS

| | | | |
|---|---|---|---|
| 3,986,868 A | 10/1976 | Crossley | |
| 4,964,967 A | 10/1990 | Hashimoto et al. | |
| 5,169,597 A | 12/1992 | Davidson et al. | |
| 5,415,704 A | 5/1995 | Davidson | |
| 5,477,864 A | 12/1995 | Davidson | |
| 5,573,401 A | 11/1996 | Davidson et al. | |
| 5,782,910 A | 7/1998 | Davidson | |
| 5,871,595 A * | 2/1999 | Ahmed et al. | 148/421 |
| 6,607,693 B1 * | 8/2003 | Saito et al. | 420/417 |
| 6,767,418 B1 * | 7/2004 | Zhang et al. | 148/421 |
| 6,913,546 B2 | 7/2005 | Kakiuchi | |
| 2002/0033717 A1 | 3/2002 | Matsuo | |
| 2004/0158309 A1 * | 8/2004 | Wachter et al. | 623/1.13 |
| 2005/0074357 A1 | 4/2005 | Steinemann | |
| 2007/0193662 A1 | 8/2007 | Jablokov et al. | |
| 2007/0227628 A1 * | 10/2007 | Koyanagi et al. | 148/407 |
| 2009/0060777 A1 | 3/2009 | Maeda et al. | |
| 2009/0130632 A1 | 5/2009 | Tsuru et al. | |
| 2009/0139617 A1 | 6/2009 | Steinemann | |
| 2009/0220811 A1 * | 9/2009 | Miyazaki et al. | 428/544 |
| 2011/0070121 A1 | 3/2011 | Lee et al. | |

FOREIGN PATENT DOCUMENTS

| | | |
|---|---|---|
| DE | 19935935 A1 | 2/2000 |
| EP | 0 640 353 | 3/1995 |
| EP | 0 707 085 | 4/1996 |
| EP | 1 878 808 | 1/2008 |
| EP | 1 743 045 | 2/2008 |
| EP | 1 961 430 | 8/2008 |

(Continued)

OTHER PUBLICATIONS

Daisuke Kuroda et al., "Design and Mechanical Properties of New β Type Titanium Alloys for Implant Materials," Materials Science and Engineering A243 (1998) pp. 244-249.

(Continued)

*Primary Examiner* — John J Zimmerman
(74) *Attorney, Agent, or Firm* — Morgan, Lewis & Bockius LLP

(57) ABSTRACT

An alloy having from about 5 to about 15 wt % Ta, from 0 to about 5 wt % Nb, from about 0.5 to about 15 wt % Zr, and the balance Ti is disclosed. The alloy is particularly intended for medical devices, such as implants for the body.

18 Claims, 3 Drawing Sheets

FOREIGN PATENT DOCUMENTS

| | | | |
|---|---|---|---|
| JP | 61-174346 | | 8/1986 |
| JP | 2000102602 A | | 4/2000 |
| JP | 2001-003126 | * | 1/2001 |
| JP | 2001-003127 | * | 1/2001 |
| JP | 2006-89826 | | 4/2006 |
| KR | 20020047981 A | | 6/2002 |
| KR | 100393270 | | 7/2003 |
| WO | 95/34251 | | 12/1995 |
| WO | WO 2005/106056 | | 11/2005 |

OTHER PUBLICATIONS

Atsushi Sugino et al., "Effect of Spatial Design and Thermal Oxidation on Apatite Formation on Ti-15Zr-4Ta-4Nb alloy", *Acta Biomaterial* 5 (2008) pp. 298-304.

* cited by examiner

TITANIUM-BASED ALLOY

RELATED APPLICATION DATA

This application claims priority under 35 U.S.C. §119 and/or §365 to EP Application No. 08 16 4918, filed Sep. 23, 2008, the entire contents of which are incorporated herein by reference.

FIELD

The present disclosure relates to a titanium-based alloy. It further relates to a method of its preparation. Finally, the present disclosure relates to products such as medical devices composed of the alloy.

BACKGROUND

Examples of applications for titanium alloys are such where light weight in combination with high strength is needed. Furthermore, titanium alloys are generally corrosion resistant and have good high temperature properties. Examples of applications are found in the aerospace-, chemical-, and automotive industries, in the field of sports and leisure, and in the medical field.

The most widely used titanium alloy overall is Ti-6Al-4V. It is an alpha+beta alloy which has a good balance of mechanical properties.

Titanium and titanium alloys are since a long time being used in medical devices such as implants for the human body. Such implants are, for example, hip joint prostheses, knee joint prostheses, spinal implants, bone plate systems, intramedullary nails, dental implants, cardiovascular implants, ear-implants, and nose-implants. Pure titanium is at present to a great extent used and has excellent biocompatibility but has drawbacks in some applications due to its mechanical properties such as strength. The alloy Ti-6Al-4V has good mechanical properties such as high strength, and has also excellent biocompatibility. It has therefore been used as an alternative to pure titanium. However, there is a growing concern about the risks of exposing the human body to aluminium and vanadium. It would therefore be desirable to find alternative alloys not containing these elements, while still having excellent, or even improved, mechanical properties, and excellent biocompatibility. Such an alloy would also find use in non-medical applications as an alternative to Ti-6Al-4V.

There is a need for titanium-based alloys which are not based on aluminium and/or vanadium, especially useful for medical implants, and which especially have mechanical properties, such as hardness, on the same level as, or better than, Ti-6Al-4V.

EP 0 707 085 A1 discloses a biocompatible alloy of Ti containing 2.5-13 wt % Zr, 20-40 wt % Nb and 4.5-25 wt % Ta. The ratio of Nb/Ta is between 2 and 13. Preferred alloys are Ti-12.4Ta-29.2Nb-7.1Zr, Ti-21.6Ta-23.8Nb-4.6Zr, and Ti-5.7Ta-35.3Nb-7.3Zr.

U.S. Pat. No. 5,169,597 discloses a biocompatible titanium alloy containing either 10-20 wt % Nb or 35-50 wt % Nb, and 13-20 wt % Zr.

EP 0 640 353 A1 discloses a surface and near surface hardened implant of titanium alloys comprising a core of a titanium alloy containing either 10-20 wt % Nb or 35-50 wt % Nb, and 0.5-20 wt % Zr.

U.S. Pat. No. 5,415,704 discloses an alloy of Ti—Nb—Zr with less than 2 wt % of a solute of, e.g., Ta.

Kuroda et al., "Design and mechanical properties of new beta type titanium alloys for implant materials", Materials Science and Engineering A243, 244-249, 1998, discloses an alloy Ti-13Ta-29Nb-4.6Zr.

Many of the prior art alloys containing titanium for implant purposes contain comparatively low atomic percentage of titanium.

SUMMARY

It would be desired to provide a titanium alloy which has a high content of titanium in order to keep the desired properties of pure titanium, e.g. biocompatibility and light weight.

It is therefore an object of the present invention to provide a titanium-based alloy which has excellent mechanical properties such as high hardness and which is not based on aluminium and vanadium as alloying elements. Other desired properties of the alloy are good oxide-forming properties, e.g. ability to form rutile and/or anatase on the surface, and also good apatite-formation ability.

Exemplary embodiments of an alloy comprise from about 5 to about 15 wt % Ta, from 0 to about 5 wt % Nb, from about 0.5 to about 15 wt % Zr, and the balance Ti and incidental impurities.

Exemplary embodiments of a method for preparing an alloy comprising from about 5 to about 15 wt % Ta, from 0 to about 5 wt % Nb, from about 0.5 to about 15 wt % Zr, and the balance Ti and incidental impurities, comprise melting together the elements Ti, Ta, Zr, and optionally Nb, followed by cooling to solidify the alloy formed.

It is to be understood that both the foregoing general description and the following detailed description are exemplary and explanatory and are intended to provide further explanation of the invention as claimed.

DETAILED DESCRIPTION

Figure 1:
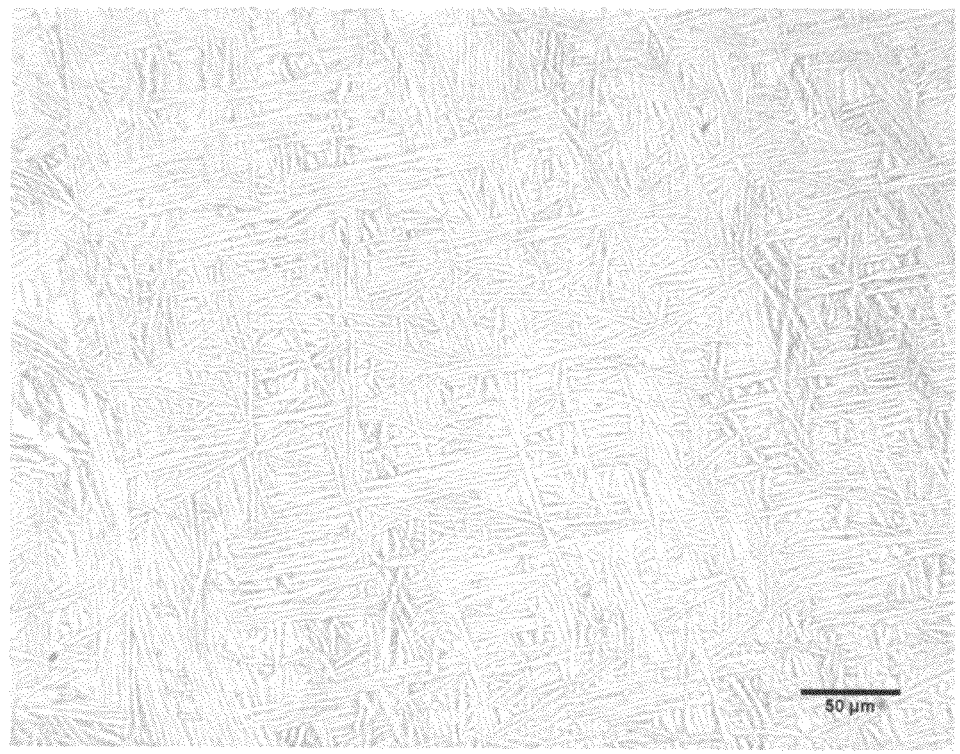
FIGS. 1-5 show LOM (light optical microscopy) pictures of the microstructure of heat treated alloys according to the invention. A mixture of alpha phase (light areas) and beta phase (dark areas) is seen.

The present invention provides an alloy comprising from about 5 to about 15 wt % Ta, from 0 to about 5 wt % Nb, from about 0.5 to about 15 wt % Zr, and the balance Ti and incidental impurities.

The present invention also provides a method for preparing the alloy comprising of from about 5 to about 15 wt % Ta, from 0 to about 5 wt % Nb, from about 0.5 to about 15 wt % Zr, and the balance Ti and incidental impurities, comprising melting together the elements Ti, Ta, Zr, and optionally Nb, followed by cooling to solidify the alloy formed.

Suitably, the alloy comprises from about 7 to about 13 wt % Ta, preferably from about 9 to about 11 wt % Ta.

In one embodiment, the alloy is substantially free from Nb, i.e. comprises less than about 0.1 wt % Nb, preferably less than about 0.05 wt % Nb.

In one embodiment, the alloy comprises from about 0.1 to about 4 wt % Nb, preferably from about 0.5 to about 3 wt % Nb, most preferably from about 1 to about 2 wt % Nb.

Suitably, the alloy comprises from about 0.8 to about 12 wt % Zr, preferably from about 1 to about 10 wt % Zr, more preferably from about 1.5 to about 5 wt % Zr.

In one embodiment, the alloy comprises about 10.3 wt % Ta, about 1.6 wt % Nb, about 1.7 wt % Zr, and the balance Ti and incidental impurities.

In one embodiment, the alloy comprises about 10.3 wt % Ta, about 1.6 wt % Nb, about 8 wt % Zr, and the balance Ti and incidental impurities.

In one embodiment, the weight ratio Nb/Ta is substantially 0, i.e. less than about 0.05, preferably less than about 0.03.

In another embodiment, the weight ratio Nb/Ta is from about 0.05 to about 1, preferably from about 0.05 to about 0.5, preferably from about 0.075 to about 0.5, more preferably from about 0.1 to about 0.5, most preferably from about 0.1 to about 0.2.

The content of the sum of Ta and Nb in the alloy is suitably from about 6 to about 20 wt %, preferably from about 7 to about 16 wt %, more preferably from about 8 to about 14 wt %, most preferably from about 9 to about 12 wt %.

The content of the sum of Ta, Nb and Zr in the alloy is suitably from about 7 to about 35 wt %, preferably from about 8 to about 30 wt %, more preferably from about 9 to about 25 wt %, even more preferably from about 10 to about 20 wt %, most preferably from about 12 to about 15 wt %.

The content of the sum of Ti and Zr in the alloy is suitably from about 80 to about 95 wt %, preferably from about 85 to about 94 wt %.

The content of the sum of Ti and Zr in the alloy is suitably from about 90 to about 98.5 at %, preferably from about 92 to about 98 at %, most preferably from about 94 to about 97 at %.

The content of Ti in the alloy is suitably from about 65 to about 93 wt %, preferably from about 70 to about 93 wt %, preferably from about 70 to about 92 wt %, more preferably from about 75 to about 91 wt %, more preferably from about 75 to about 91 wt %, even more preferably from about 80 to about 90 wt %, most preferably from about 85 to about 88 wt %.

The content of Ti in the alloy is suitably at least about 80 at %, preferably at least 85 at %, most preferably at least 90 at %.

The content of Ti in the alloy is suitably from about 80 to about 98 at %, preferably from about 85 to about 97 at %, most preferably from about 90 to about 96 at %.

The content of beta-phase in the alloy is suitably at least about 10 vol %, preferably at least about 20 vol %. The linear intercept method is suitably used for determining the content of beta-phase.

In one embodiment, the alloy is an alpha+beta alloy wherein the content of beta-phase in the alloy is suitably from about 10 to about 60 vol %, preferably from about 20 to about 55 vol %. In one embodiment the alpha+beta alloy is an alpha1+alpha2+beta alloy, wherein alpha1 is a primary alpha phase and alpha2 is a secondary alpha phase.

In another embodiment the alloy is a meta-stable beta alloy having substantially no alpha phase present.

The hardness of the alloy, according to Vickers hardness test, is suitably at least about 250 HV3, or from about 250 to about 650 HV3, preferably at least about 300 HV3, or from about 300 to about 550 HV3, most preferably at least about 350 HV3, or from about 350 to about 450 HV3.

Incidental impurities may be, for example, nitrogen, carbon, hydrogen and oxygen. The total content of incidental impurities in the alloy is suitably less than 0.5 wt %, preferably less than 0.1 wt %.

The method for preparing the alloy suitably comprises arc melting of the alloy elements, preferably under vacuum.

The method for preparing the alloy suitably further comprises heat treatment of the solidified alloy. The heat treatment comprises heating the alloy to a temperature of suitably from about 500 to about 1000° C., preferably from about 550 to about 950° C., more preferably from about 600 to about 900° C., most preferably from about 700 to about 850° C. The heat treatment is suitably carried out in an inert gas or vacuum. The duration of the heat treatment is suitable at least about 0.25 hour, preferably at least about 0.5 hour, most preferably at least about 1 hour. After the heat treatment the alloy is cooled down at a rate of suitably at least about 5° C./min, preferably at least about 10° C./min, most preferably at least about 15° C./min. The cooling is suitably continued until 100° C. is reached, preferably until room temperature is reached. The cooling is preferably made by contacting the alloy with a flow of an inert gas, such as a noble gas at a flow rate and of a temperature sufficient to cool down the alloy in a desired manner. In one embodiment, a heat treatment comprises a combination of treatments at different temperatures for a certain amount of time, suitably at least 0.25 hour, preferably at least 0.5 hour, after which the alloy is cooled down. In such an embodiment, preferably a first treatment at a temperature higher than the temperature of a subsequent second heat treatment. In one embodiment a first heat treatment is made at a temperature of from about 750 to about 850° C. followed by a second heat treatment at a temperature of from about 550 to about 650° C. which is followed by cooling.

The disclosed alloy is suitably hot worked or cold worked, according to known procedures in prior art for making titanium-based alloys.

In one embodiment the method suitably further comprises oxidising the surface of the alloy.

In one embodiment the surface of the alloy according to the invention suitably comprises a crystalline oxide layer. The crystalline oxide layer suitably comprises rutile and/or anatase.

The invention also relates to the use of the alloy according to the invention in the production of a shaped body.

The invention also relates to a shaped body composed of the alloy according to the invention.

The invention also relates to a medical device composed of the alloy according to the invention.

The invention also relates to the use of the alloy according to the invention in the production of a medical device.

The medical device is suitably an implant for the human or animal body. Such an implant is, for example, a hip joint prosthesis, a knee joint prosthesis, a spinal implant, a bone plate system, an intramedullary nail, a dental implant, a cardiovascular implant, an ear-implant, and a nose-implant.

EXAMPLES

Example 1

The Invention

A Ti-alloy was made by arc-melting under vacuum Ti, Ta, Nb and Zr in the proportions: 86.4 wt % Ti, 10.3 wt % Ta, 1.6 wt % Nb, and 1.7 wt % Zr.

Example 2

The Invention

A Ti-alloy was made by arc-melting under vacuum Ti, Ta, and Zr in the proportions: 87.8 wt % Ti, 10.5 wt % Ta, and 1.8 wt % Zr.

Example 3

The Invention

A Ti-alloy was made by arc-melting under vacuum Ti, Ta, Nb and Zr in the proportions: 80.1 wt % Ti, 10.3 wt % Ta, 1.6 wt % Nb, and 8 wt % Zr.

Example 4

Reference

A Ti-alloy was made in the same way as in Example 1 using Ti, Ta, Nb and Zr in the proportions: 70.8 wt % Ti, 10.3 wt % Ta, 1.6 wt % Nb, and 17.3 wt % Zr.

Example 5

Reference

A Ti-alloy was made in the same way as in Example 1 using Ti, Ta, Nb and Zr in the proportions: 53 wt % Ti, 5 wt % Ta, 35 wt % Nb, and 7 wt % Zr. This alloy corresponds to one of the preferred ones in EP 0 707 085 A1.

Example 6

Reference

A Ti-alloy was made in the same way as in Example 1 using Ti, Ta, and Nb in the proportions: 86.7 wt % Ti, 13 wt % Ta, and 0.3 wt % Nb.

Example 7

Heat Treatment and Beta-Phase Content

In order to first homogenize the alloys made in Examples 1-6, they were heat treated (HT1) at 600° C. for 10 hours in an argon gas atmosphere. The cooling rate was about 16° C./min. Cooling was made by using a flow of argon gas of room temperature. The homogenization was succesful with a homogenously distributed microstructure. FIG. 1 shows the microstructure of a homogenized alloy according to Example 1.

Homogenized alloys were then subjected to a further heat treatment (HT2a), wherein homogenized samples of the alloys of Examples 1, 4 and 6 were subjected to 700° C., 700° C., and 715° C., respectively, for 10 hours in an argon gas atmosphere. The cooling rate was between 16 and 20° C./min.

Figure 2:
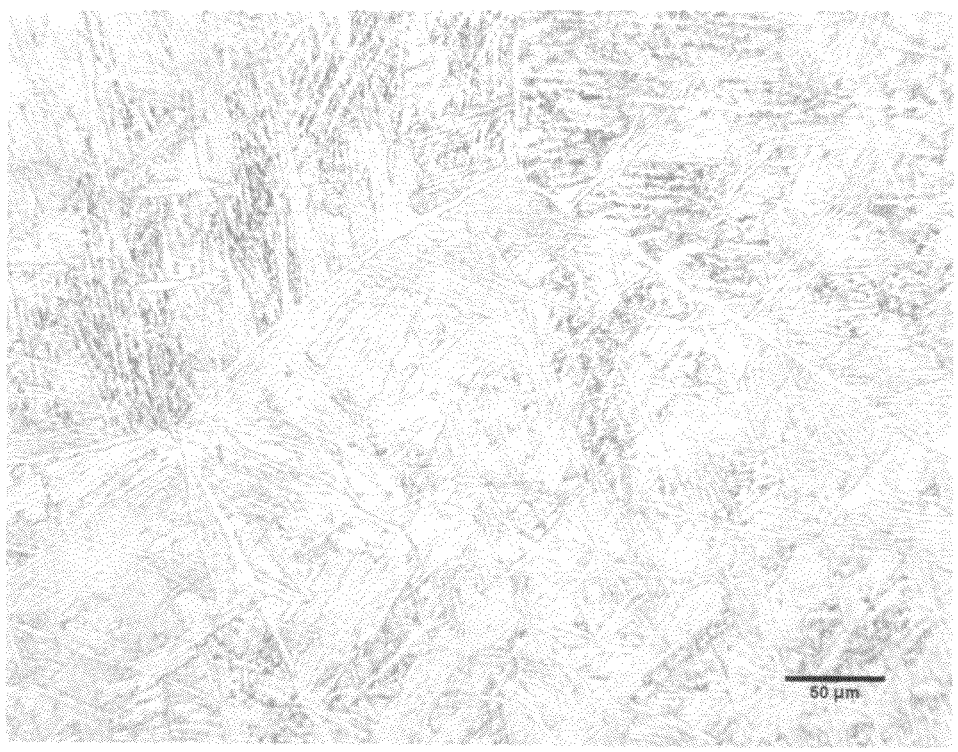

Another heat treatment (HT2b) was made, wherein homogenized samples of the alloys of Examples 1, 4 and 6 were subjected to 800° C. for 1 hour and 10 hours, respectively, in an argon gas atmosphere. The cooling rate was 20° C./min. FIG. 2 shows the microstructure of the heat treated (HT2b) alloy according to Example 1.

Figure 3:
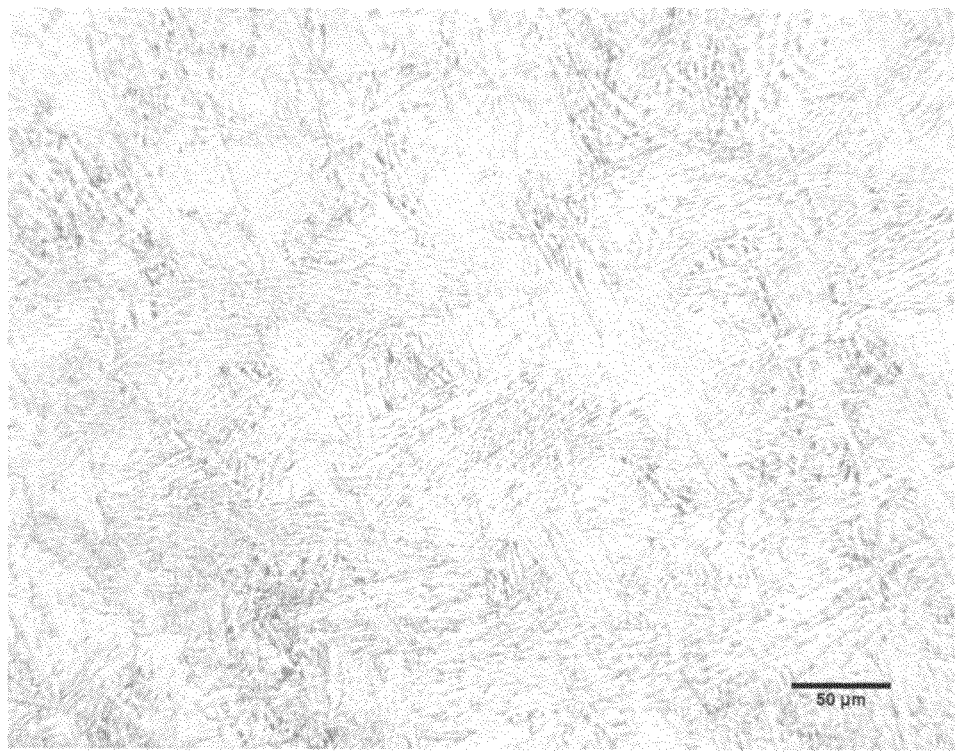
Figure 4:
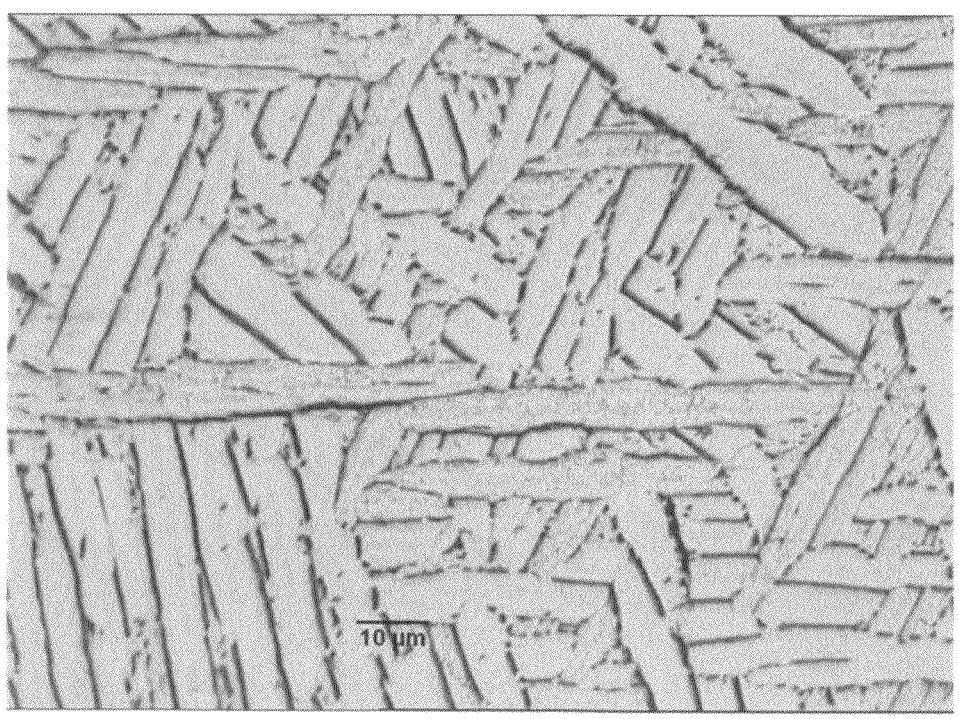
Figure 5:
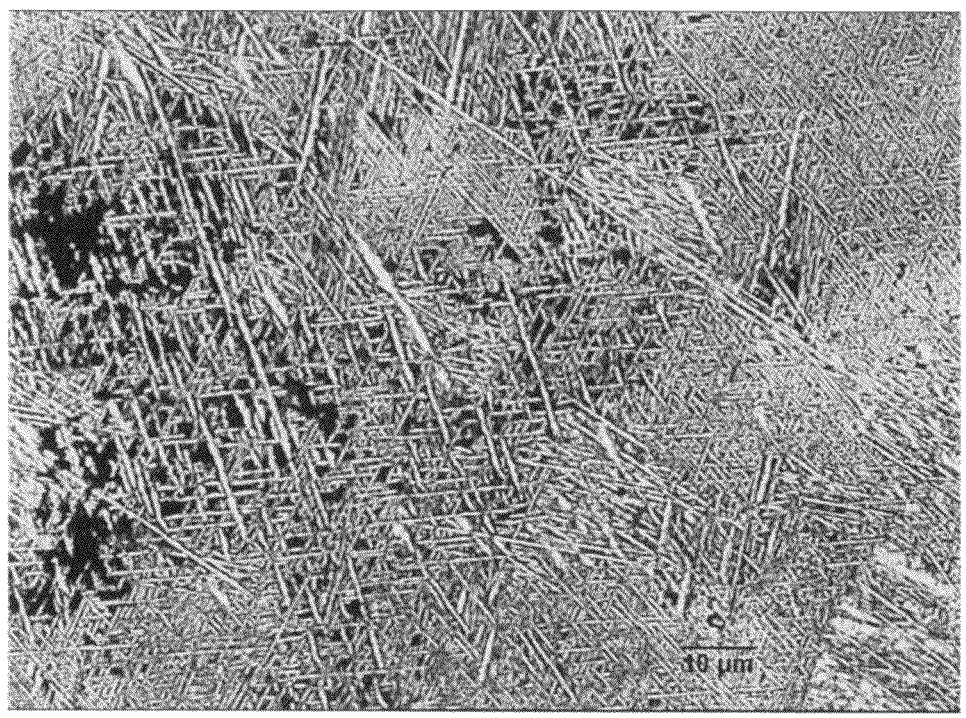

Another heat treatment (HT2c) was made, wherein a homogenized samples of the alloys of Examples 1, 2, 3 and 5 were first subjected to 800° C. for 1 hour followed by 600° C. for 4 hours, both treatments being made in an argon gas atmosphere. The cooling rate was 20 and 16° C./min respectively. FIGS. 3, 4 and 5 respectively show the microstructure of the heat treated (HT2c) alloys according to Examples 1, 2 and 3.

Studies of the effects of the different heat treatment temperatures on beta-phase content were made. As a reference a commercial Ti-6Al-4V was also analysed. Table 1 shows the results.

The beta-phase content of the alloys was determined after the homogenization heat treatment and after each individual heat treatment made by analysing LOM images of the microstructure with the linear intercept method. The method comprises using a test pattern of lines of known length randomly laid over a plane section, and measuring the individual intercept lengths across beta-phase.

TABLE 1

| Sample origin | | beta-phase (vol %) | | | |
|---|---|---|---|---|---|
| (example) | Composition | HT1 | HT2a | HT2b | HT2c |
| 1 | Ti—10.3Ta—1.6Nb—1.7Zr | 27 | 27 | 33 | 32 |
| 2 | Ti—10.5Ta—1.8Zr | —* | —* | —* | 17 |
| 3 | Ti—10.3Ta—1.6Nb—8Zr | 25 | —* | —* | —* |
| 4 | Ti—10.3Ta—1.6Nb—17.3Zr | 19 | 18 | —* | —* |
| 5 | Ti—5Ta—35Nb—7Zr | —* | —* | —* | 100**** |
| 6 | Ti—13Ta—0.3Nb | 0** | 0** | 0** | —* |
| — | Ti—6Al—4V | | | 29*** | |

*not made
**no or very small amount of beta-phase seen in microstructure images
***as received
****meta-stable beta alloy The LOM pictures (FIGS. 1-4) of the microstructure of the alloy of Example 1 after different heat treatments show a mixture of alpha phase (light areas) and beta phase (dark areas).

Example 8

Hardness

The hardness of the three alloys of Examples 1-3 after heat treatment, as well as the commercial Ti-6Al-4V alloy, and commercial pure titanium (Grade 2) were tested by using the Vickers hardness test. Also hardness values of the alloys prior to the first heat treatment were determined. Table 2 shows the results. HT1, HT2a, HT2b and HT2c=the different heat treatments 1 (homogenization), and 2a, 2b and 2c respectively.

TABLE 2

| Sample origin | | Hardness (HV3) | | | |
|---|---|---|---|---|---|
| (example) | Composition | HT1 | HT2a | HT2b | HT2c |
| 1 | Ti—10.3Ta—1.6Nb—1.7Zr | 392 | 400 | 401 | 398 |
| 2 | Ti—10.5Ta—1.8Zr | 317 | —* | —* | 320 |
| 3 | Ti—10.3Ta—1.6Nb—8Zr | 432 | —* | —* | —* |
| 4 | Ti—10.3Ta—1.6Nb—17.3Zr | 216 | 214 | —* | —* |
| 5 | Ti—5Ta—35Nb—7Zr | 223 | —* | —* | 189 |
| 6 | Ti—13Ta—0.3Nb | 143 | 146 | 143 | —* |
|  | Ti—6Al-4V |  | 354** |  |  |
|  | Ti (Grade 2) |  | 150** |  |  |

*not made
**as received

It is concluded that an alloy according to the invention can reach hardness levels in the same range, or higher than, a commercial Ti-6Al-4V alloy.

Example 9

Young's Modulus

Pieces of the alloys according to Examples 1, 2 after heat treatment HT2c, as well as pure titanium (Grade 2) were measured in respect on Young's modulus by using a CSM Instruments nano-hardness tester. A maximum load of 50 mN was applied to 5×5 (total 25) points on a polished surface of each sample. Table 3 shows the results.

TABLE 3

| Sample origin (example) |  | Indentation/Young's modulus E (GPa) |
|---|---|---|
| 1 | Ti—10.3Ta—1.6Nb—1.7Zr | 126 |
| 2 | Ti—10.5Ta—1.8Zr | 129 |
| — | Ti (Grade 2) | 131 |

It is concluded that an alloy according to the invention can have a Young's modulus similar to a commercial Ti (Grade 2).

Example 9

Oxidation Test

Pieces of the alloys according to Examples 1, 2 and pure titanium (Grade 2) were washed both in acetone and water and then subjected to an atmosphere of 10% oxygen and 90% argon, at ambient pressure, at a temperature of 800° C. for 2.5 hours. The samples were then analysed using XRD.

The results showed that the crystalline titanium oxide rutile was formed on all samples.

Example 10

Simulated Body Fluid Test

Pieces of the oxidised alloys and pure titanium (Grade 2) according to Example 9, and the pure titanium piece were washed both in acetone and water and placed in a tube filled with 25 ml of Dulbecco's Phosphate Buffer Saline (PBS) and placed in an incubator at 37° C. for 6 days. Analysis was thereafter made using SEM.

Figure 6:
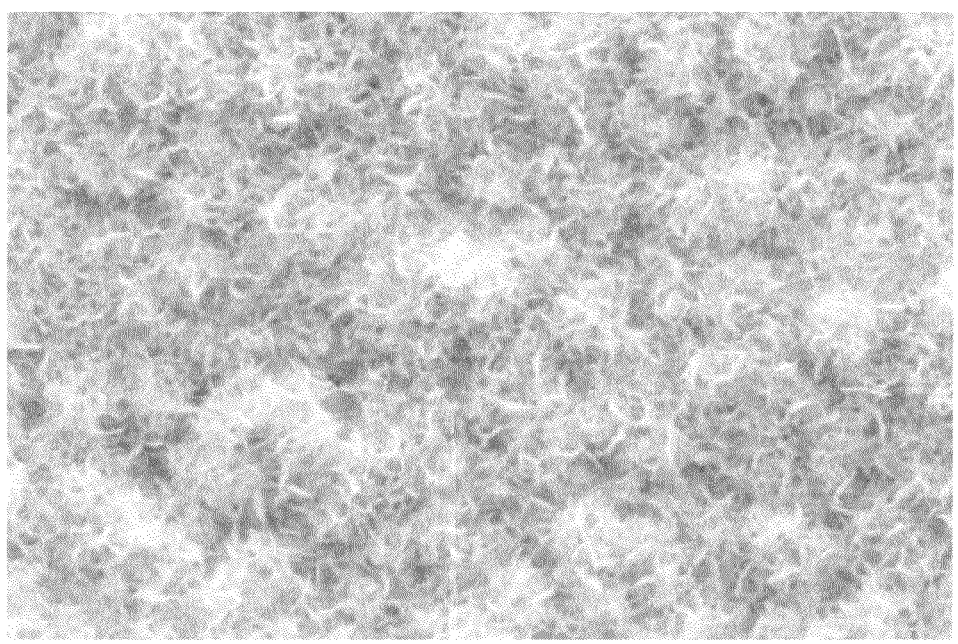
FIG. 6 shows a SEM image of the surface of the oxidised alloy from Example 1 after the SBF test.

The results showed that apatite had formed on all samples. This indicates good bioactivity. FIG. 6 shows a SEM image of surface of the oxidised alloy from Example 1 after the SBF test. A typical apatite layer is seen.

Although described in connection with preferred embodiments thereof, it will be appreciated by those skilled in the art that additions, deletions, modifications, and substitutions not specifically described may be made without department from the spirit and scope of the invention as defined in the appended claims

What is claimed is:

1. A titanium-based alloy comprising:
from 5 to 15 wt % Ta;
from 0.1 to 4 wt % Nb;
from 7 to 8 wt % Zr,
at least 65 wt % Ti; and
incidental impurities,
wherein the alloy is free of vanadium and aluminum,
wherein the alloy is an alpha+beta alloy,
wherein the content of beta-phase in the alloy is from 10 to 60 vol %, and
wherein the weight ratio Nb/Ta in the alloy is from 0.05 to 1.

2. Alloy according to claim 1, wherein the alloy comprises from 7 to 13 wt % Ta, and from 0.5 to 3 wt % Nb.

3. Alloy according to claim 1, wherein Ta is present in an amount of 10.3 wt % and Nb is present in an amount of 1.6 wt %.

4. Alloy according to claim 1, wherein the content of Ti in the alloy is at least 75 wt %.

5. Alloy according to claim 1, wherein the content of Ti in the alloy is at least 85 at %.

6. Alloy according to claim 1, wherein the hardness of the alloy, according to Vickers hardness test, is at least 250 HV3.

7. Alloy according to claim 1, wherein the surface of the alloy comprises a crystalline oxide layer.

8. Medical device composed of the alloy according to claim 1.

9. Medical device according to claim 8, which is an implant for the human or animal body.

10. Alloy according to claim 1, wherein a sum of Ta, Nb and Zr in the alloy is up to 25 wt %.

11. Alloy according to claim 10, wherein a sum of Ta, Nb and Zr in the alloy is up to 20 wt %.

12. Method for preparing an alloy comprising from 5 to 15 wt % Ta, from 0.1 to 4 wt % Nb, from 7 to 8 wt % Zr, at least 65 wt % Ti and incidental impurities, comprising melting together the elements Ti, Ta, Zr, and Nb, followed by cooling to solidify the alloy formed,
wherein the alloy is free of vanadium and aluminum,
wherein the alloy is an alpha+beta alloy,
wherein the content of beta-phase in the alloy is from 10 to 60 vol %, and
wherein the weight ratio Nb/Ta in the alloy is from 0.05 to 1.

13. Method according to claim 12, wherein the alloy comprises about 10.3 wt % Ta, and about 1.6 wt % Nb.

14. Method according to claim 12, wherein the content of Ti in the alloy is at least 75 wt %.

15. Method according to claim 12, wherein the content of Ti in the alloy is at least 85 at %.

16. Method according to claim 12, wherein the hardness of the alloy, according to Vickers hardness test, is at least about 250 HV3.

17. Method according to claim 12, further comprising heat treatment of the solidified alloy, comprising heating the alloy to a temperature of from about 500 to about 1000° C., the duration of the heat treatment is at least about 0.25 hour, whereafter the alloy is rapidly cooled down at a rate of at least about 5° C./min until room temperature is reached.

18. Method according to claim 12, further comprising oxidising the surface of the alloy.

\* \* \* \* \*